(12) United States Patent
Johnson

(10) Patent No.: US 8,331,525 B2
(45) Date of Patent: Dec. 11, 2012

(54) CHARACTERISTIC X-RAY COMPUTED LAMINOGRAPHY SYSTEM FOR HOME MADE EXPLOSIVES (HME) DETECTION

(75) Inventor: Gregory A. Johnson, Camarillo, CA (US)

(73) Assignee: Pratt & Whitney Rocketdyne, Inc., Canoga Park, CA (US)

( * ) Notice: Subject to any disclaimer, the term of this patent is extended or adjusted under 35 U.S.C. 154(b) by 1471 days.

(21) Appl. No.: 11/865,111

(22) Filed: Oct. 1, 2007

(65) Prior Publication Data

US 2012/0288059 A1    Nov. 15, 2012

(51) Int. Cl.
  *G01N 23/00* (2006.01)
  *G01N 23/04* (2006.01)
  *G01N 23/06* (2006.01)

(52) U.S. Cl. .................... 378/2; 378/57; 378/53

(58) Field of Classification Search ............... 378/2, 57, 378/149, 86; 250/358.1
See application file for complete search history.

(56) References Cited

U.S. PATENT DOCUMENTS

| | | | |
|---|---|---|---|
| 3,662,882 A * | 5/1972 | Obermayer | 378/45 |
| 4,603,257 A | 7/1986 | Packer et al. | |
| 4,821,511 A | 4/1989 | Felix et al. | |
| 4,904,084 A | 2/1990 | Geary | |
| 5,199,054 A | 3/1993 | Adams et al. | |
| 5,242,007 A | 9/1993 | Remmers et al. | |
| 5,583,904 A | 12/1996 | Adams | |
| 5,592,562 A | 1/1997 | Rooks | |
| 5,687,209 A | 11/1997 | Adams | |
| 5,719,952 A | 2/1998 | Rooks | |
| 5,742,660 A | 4/1998 | Majewski et al. | |
| 6,205,195 B1 * | 3/2001 | Lanza | 376/157 |
| 6,222,903 B1 | 4/2001 | Kim et al. | |
| 6,229,872 B1 | 5/2001 | Amos | |
| 6,324,249 B1 | 11/2001 | Fazzio | |
| 6,819,739 B2 | 11/2004 | Eppler | |
| 6,965,662 B2 | 11/2005 | Eppler et al. | |
| 6,977,985 B2 | 12/2005 | Bohn et al. | |
| 7,012,987 B1 | 3/2006 | Annis | |
| 7,023,950 B1 | 4/2006 | Annis | |
| 7,050,535 B2 | 5/2006 | Georgeson et al. | |
| 7,136,453 B2 * | 11/2006 | Jupp et al. | 378/87 |
| 2002/0031202 A1 * | 3/2002 | Callerame et al. | 378/57 |
| 2006/0093088 A1 * | 5/2006 | Sowerby et al. | 378/63 |

* cited by examiner

*Primary Examiner* — Irakli Kiknadze
(74) *Attorney, Agent, or Firm* — Carlson, Gaskey & Olds PC

(57) ABSTRACT

A homemade explosives (HME) detection system provides a coded-source, x-ray computed laminography imaging system which detects material composition by the ratio of the transmitted characteristic X-rays within a coded x-ray beam. Motion-free 3-Dimensional geometrical details are obtained through computed laminography imaging techniques.

15 Claims, 3 Drawing Sheets

CHARACTERISTIC X-RAY COMPUTED LAMINOGRAPHY SYSTEM FOR HOME MADE EXPLOSIVES (HME) DETECTION

BACKGROUND OF THE INVENTION

The present invention relates to a homemade explosives (HME) detection system, and more particularly to a Characteristic X-ray computed laminography system for HME detection.

With recent terrorist activities the potential for a terrorist to smuggle homemade explosives (HME) aboard a civilian aircraft or other mode of transit poses a real threat with severe consequences. Active X-ray radiography systems form a 2D transmission image of a container's contents, but suffer from the need of a human operator to interpret the image. Chemical detection systems, such as mass spectrometry, can provide additional information about a container's contents but suffer from the need to sample the containers contents—in turn bogging-down the transit system.

Accordingly, it is desirable to provide a homemade explosive (HME) detection system which automatically detects HME to minimize the burden of the human operator.

SUMMARY OF THE INVENTION

The homemade explosives (HME) detection system according to the present invention provides a fast, coded-source, x-ray computed laminography imaging system. The system detects material composition by the ratio of the transmitted characteristic X-rays within a coded x-ray beam. Motion-free 3-Dimensional geometrical details are obtained through computed laminography imaging techniques.

The HME system can be deployed in much the same manner that carry-on screeners are deployed today. The ability to automatically detect HME greatly relieves the burden of the human operator, greatly improves the reliability of the screening process and greatly reduces the threat of a terrorist smuggling HME aboard a civilian aircraft or other mass transit vehicles.

The present invention therefore provides a homemade explosive (HME) detection system which automatically detects HME to minimize the burden of the human operator.

BRIEF DESCRIPTION OF THE DRAWINGS

The various features and advantages of this invention will become apparent to those skilled in the art from the following detailed description of the currently disclosed embodiment. The drawings that accompany the detailed description can be briefly described as follows.

DETAILED DESCRIPTION OF THE DISCLOSED EMBODIMENT

Figure 1:
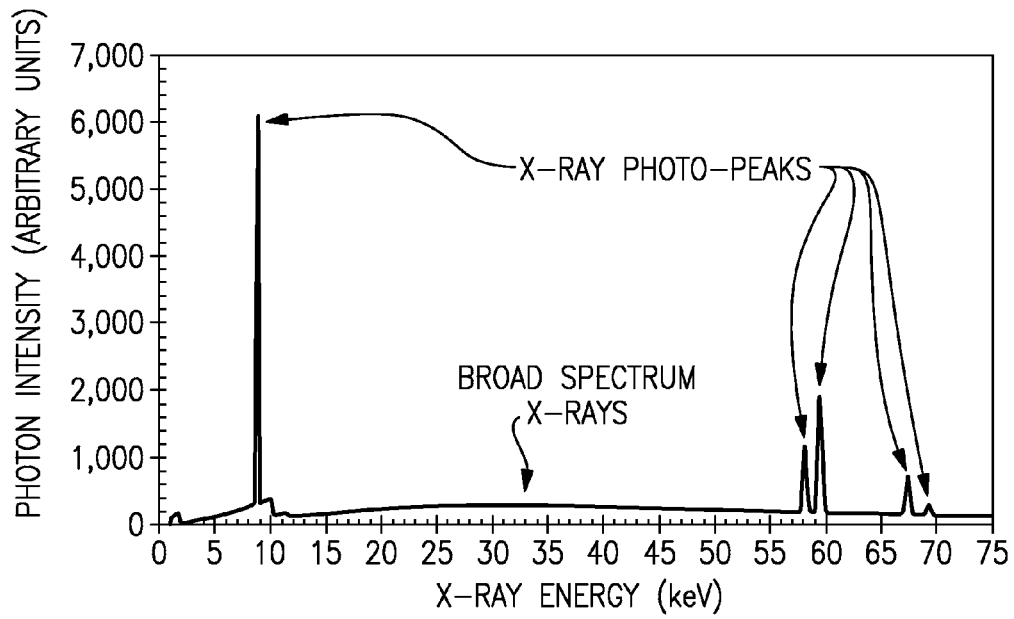
FIG. 1 is a X-ray spectrum from electrons impinging on tungsten.

X-ray generation technology has been around for many years and is very mature. X-rays are generated by accelerating electrons and impinging them on a thin metal plate; typically tungsten. X-rays emitted in a broad spectrum produce distinct photo-peaks or characteristic X-rays (see FIG. 1 for elemental tungsten). These characteristic X-rays are dependent on the electronic structure of the metal atoms in the plate. By measuring the transmission of the characteristic X-rays through an object, information regarding the objects elemental composition can be obtained.

Further, the Characteristic X-rays can be tailored to meet the particular needs at desired ranges. By using alloys or powder metallurgy, elements can be combined to give characteristic X-rays in a desired range. For instance, 50/50 Moly-Rhenium generates photo-peaks in the 17 & 19 keV range as well as the 60 & 70 keV range. A tungsten-silver combination generates photo-peaks in the 22 & 25 keV range. Characteristic X-ray transmission radiography forms an image showing both the density and material composition by measuring the attenuation of the characteristic X-rays contained in an x-ray beam along straight paths from the radiation source.

By utilizing a coded-source, 3-Dimensional coded images are obtained by employing computed laminography techniques. Coded imaging is widely used in observational astronomy and medical imaging (e.g. emission images) and is gaining favor in the neutron imaging field. A ratio, R, of the low-energy and high-energy x-ray attenuation coefficients can be calculated directly from the ratio of the transmitted low-energy and high energy characteristic X-rays as follows:

$$R = \frac{\mu_{le}}{\mu_{he}} = \frac{\ln(I_{le}/I_{le}^0)}{\ln(I_{he}/I_{he}^0)} \quad \text{(equation 1)}$$

where $\mu$ is the mass attenuation coefficient, I is characteristic X-ray intensity and the subscripts le and he are for low energy and high-energy characteristic X-rays respectively.

Figure 2:
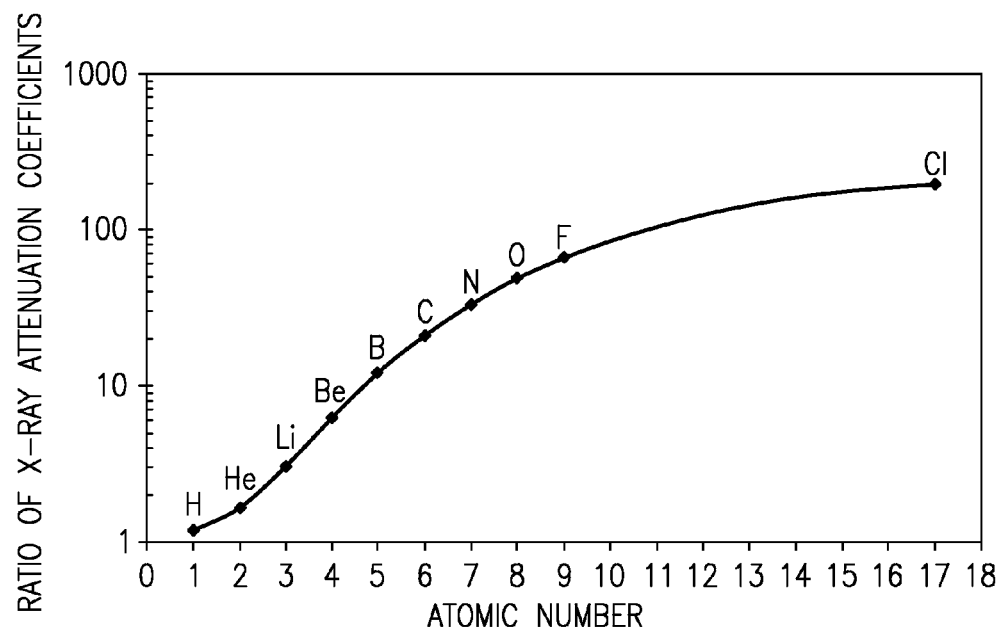
FIG. 2 is a calculated ratio, R, of the 8.8 keV to the 60 keV characteristic X-ray attenuation coefficients for the light elements.
Figure 3:
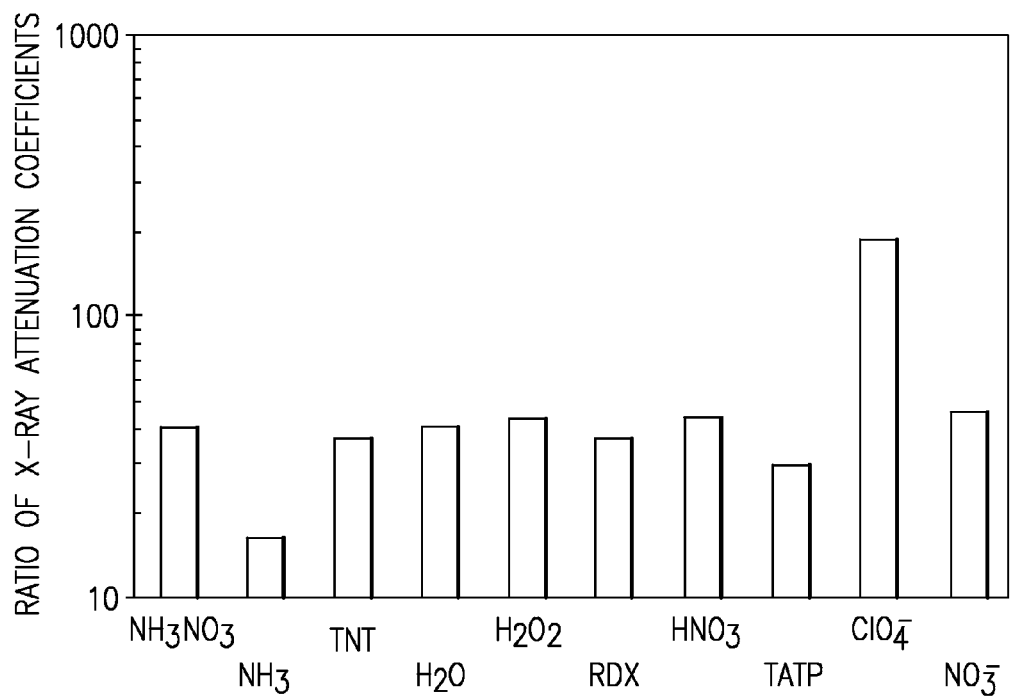
FIG. 3 is a Calculated ratio, R, of the 8.8 keV to the 60 keV characteristic X-ray attenuation coefficient for a few selected explosives, fuels and oxidizers.

The ratio R can therefore be determined directly from the measured transmission of the low-energy and high energy characteristic X-rays without knowledge of the mass of material in the radiation beam path. Ratio R thereby provides a powerful discriminator for different classes of materials (FIG. 2 illustrates the dependence of this ratio on elemental composition for 8.8 keV characteristic X-ray and 60 keV characteristic X-ray). Low Z elements have the lowest R values increasing rapidly with increasing atomic number. To further illustrate the utility of this method for detecting HME, the R values for a few selected explosives, fuels and oxidizers are shown in FIG. 3.

Arranging the x-ray source in a uniformly redundant array (URA), a precise mathematical construct which allows rapid image reconstruction, and coupling it to imaging plates results in an x-ray coded-source radiography system. Coding of the X-ray source is accomplished in at least one of two ways: 1) by applying a shield mask to a planar x-ray source in which the shield mask contains apertures arranged in a uniformly redundant array (URA) or a modified uniformly redundant array (MURA); or 2) by internal arrangement of the x-ray generator itself.

Figure 4:
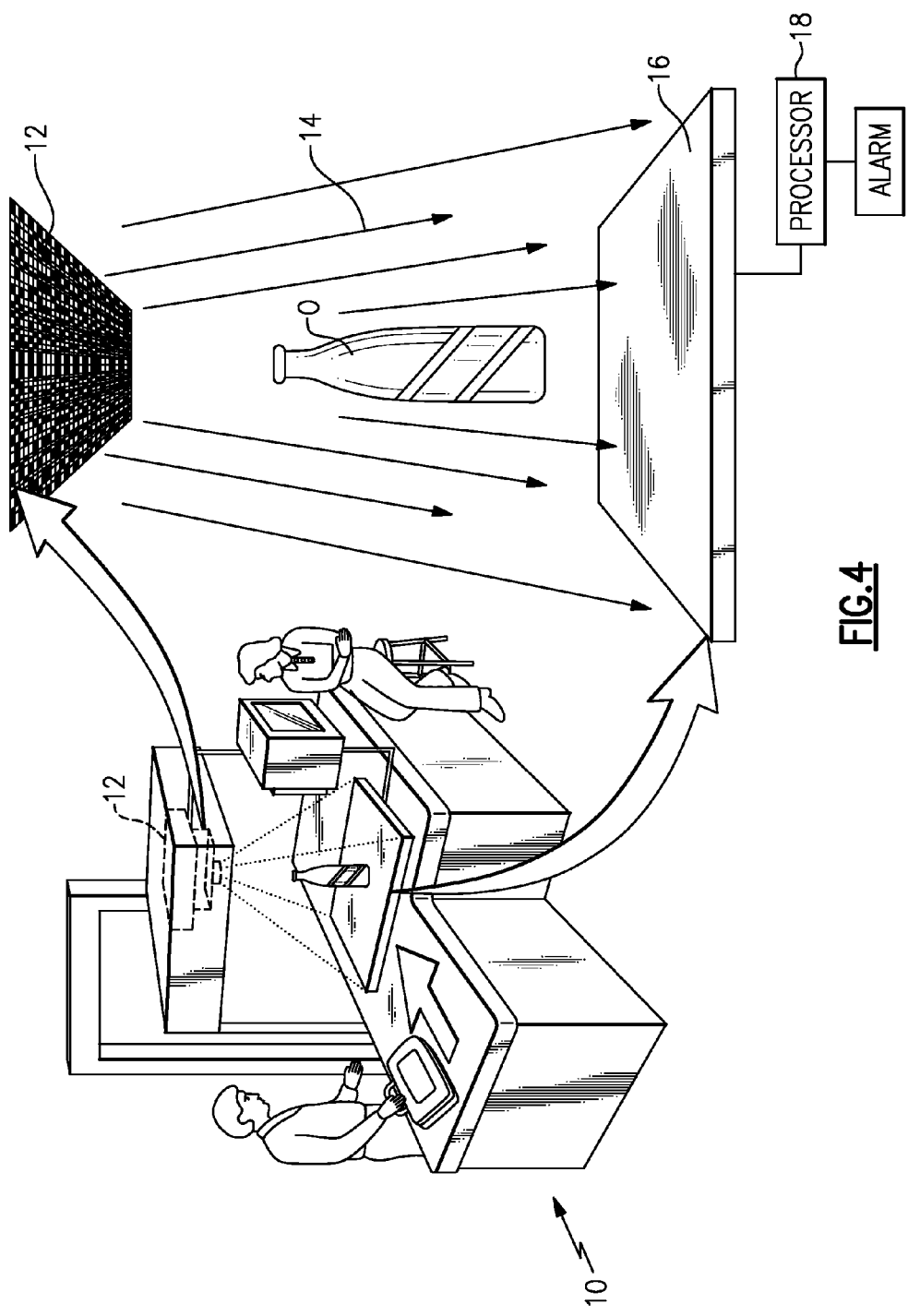
FIG. 4 is a block diagram of a homemade explosives (HME) detection system.

Referring to FIG. 4, a homemade explosives (HME) detection system 10 is schematically illustrated. A coded X-ray source 12 forms a coded beam 14 which illuminates an object O to be interrogated. The transmission of the characteristic X-rays "shining" through an object are measured on an X-ray detector array 16 such that the transmission of the different characteristic X-rays reveal the elemental composition of the materials contain in the object being interrogated. One such X-ray detector array includes a CCD which digitizes the image for communication to a microprocessor system 18 for the requisite analysis.

The Characteristic X-rays interact with the interrogated object in accordance with its composition and density. Uncollided x-rays emerge from the interrogated object O on their original beam paths upon the X-ray detector array 16 for discrimination by the microprocessor system 18. In this way, only x-rays transmitted through the object O produce a coded image. By determining the ratio of the transmitted characteristic X-ray coded images, a coded R-value image is obtained which reveals information about the material composition of the interrogated object O. Further, because of the coded X-ray source 12, and because reconstruction methods therefor are almost identical to coded apertures, motionless 3-Dimensional imaging through, for example, laminography may then be utilized by the microprocessor system 18. Laminography is the reconstruction of the planes or layers perpendicular to the beam. These planes are reconstructed by the microprocessor system 18 to reveal the 3D imagery via laminography. In this manner, hidden explosives, flammable liquids or strong oxidizers can be revealed and distinguished from benign substances.

The microprocessor system 18 typically includes a processing module, such as a microprocessor and a memory device in communication therewith. The system stores data and control algorithms in the memory device or other suitable memory location. The memory device may, for example, include RAM, ROM, DVD, CD, a hard drive, or other electronic, optical, magnetic, or any other computer readable medium onto which is stored the data and control algorithms described herein. The control algorithms are the scheme by which the decisions are made. It should be understood that various systems may be utilized to perform the laminography.

It should be understood that relative positional terms such as "forward," "aft," "upper," "lower," "above," "below," and the like are with reference to the normal operational attitude of the vehicle and should not be considered otherwise limiting.

It should be understood that although a particular component arrangement is disclosed in the illustrated embodiment, other arrangements will benefit from the instant invention.

Although particular step sequences are shown, described, and claimed, it should be understood that steps may be performed in any order, separated or combined unless otherwise indicated and will still benefit from the present invention.

The foregoing description is exemplary rather than defined by the limitations within. Many modifications and variations of the present invention are possible in light of the above teachings. The disclosed embodiments of this invention have been disclosed, however, one of ordinary skill in the art would recognize that certain modifications would come within the scope of this invention. It is, therefore, to be understood that within the scope of the appended claims, the invention may be practiced otherwise than as specifically described. For that reason the following claims should be studied to determine the true scope and content of this invention.

What is claimed is:

1. A homemade explosives (HME) detection system comprising:
    a coded X-ray source to illuminate an object with a coded X-ray beam;
    an X-ray detector array which receives said coded X-ray beam, the object located between the coded X-ray source and the X-ray detector array such that characteristic X-rays emerge from the object for discrimination by the X-ray detector array; and
    a microprocessor system in communication with the X-ray detector array which measures transmission of the characteristic X-rays through the object to reveal an elemental composition of the object.

2. The system as recited in claim 1, wherein said coded X-ray source produces said coded X-ray beam with a shield mask.

3. The system as recited in claim 2, wherein said shield mask contains apertures arranged in a uniformly redundant array (URA).

4. The system as recited in claim 2, wherein said shield mask contains apertures arranged in a modified uniformly redundant array (MURA).

5. The system as recited in claim 2, wherein said microprocessor system determines a ratio R of the low-energy and high-energy x-ray attenuation coefficients directly from the ratio of the transmitted low-energy and high energy characteristic X-rays according to the formula as follows:

$$R = \frac{\mu_{le}}{\mu_{he}} = \frac{\ln(I_{le}/I_{le}^0)}{\ln(I_{he}/I_{he}^0)}$$

where $\mu$ is the mass attenuation coefficient, I is characteristic X-ray intensity and the subscripts le and he are for low energy and high-energy characteristic X-rays respectively.

6. The system as recited in claim 5, wherein said microprocessor system utilizes said ratio R as a discriminator for different classes of materials.

7. The system as recited in claim 1, wherein said coded X-ray source produces said coded X-ray beam by an internal arrangement.

8. The system as recited in claim 1, wherein the coded X-ray source produces said coded X-ray beam with a shield mask having apertures arranged in an array.

9. A method of determining a material composition of an object comprising the steps of:
    (A) illuminating an object with a coded X-ray beam; and
    (B) detecting a material composition of the object by a ratio of transmitted characteristic X-rays passed through the object.

10. A method as recited in claim 9, further comprising the step of:
    (C) determining geometrical details of the object through a computed laminography imaging technique from the coded x-ray beam.

11. A method as recited in claim 9, wherein said step (B) further comprises:
    (a) detecting selected compositions within the object.

12. A method as recited in claim 9, wherein said step (B) further comprises:
    (a) utilizing a ratio R as a discriminator for different classes of materials, a ratio R of the low-energy and high-energy x-ray attenuation coefficients directly from the ratio of the transmitted low-energy and high energy characteristic X-rays according to the formula as follows:

$$R = \frac{\mu_{le}}{\mu_{he}} = \frac{\ln(I_{le}/I_{le}^0)}{\ln(I_{he}/I_{he}^0)}$$

where $\mu$ is the mass attenuation coefficient, I is characteristic X-ray intensity and the subscripts le and he are for low energy and high-energy characteristic X-rays respectively.

13. A method as recited in claim 9, wherein the coded X-ray beam is provided utilizing a shield mask having an array of apertures.

14. A method of determining a homemade explosive (HME) comprising the steps of:
(A) illuminating an object with a coded X-ray beam; and
(B) detecting a material composition of the object by a ratio of transmitted characteristic X-rays passed through the object; and
(C) utilizing the ratio R as a discriminator for the material composition within the object.

15. The method of claim 14, wherein the coded X-ray beam is provided utilizing a shield mask having an array of apertures.

* * * * *